US009492437B2

(12) United States Patent
Stechl et al.

(10) Patent No.: US 9,492,437 B2
(45) Date of Patent: Nov. 15, 2016

(54) OTAMIXABAN FOR TREATMENT OF ELDERLY AND RENAL IMPAIRED NON-ST ELEVATION MYOCARDIAL INFARCTION PATIENTS

(75) Inventors: Jens Stechl, Frankfurt am Main (DE); Angele Moryusef, Bridgewater, NJ (US); Christophe Gaudin, Paris (FR); Pascale Ythier-Moury, Paris (FR)

(73) Assignee: SANOFI, Paris (FR)

( * ) Notice: Subject to any disclaimer, the term of this patent is extended or adjusted under 35 U.S.C. 154(b) by 665 days.

(21) Appl. No.: 13/387,639

(22) PCT Filed: Jul. 22, 2010

(86) PCT No.: PCT/EP2010/060615
§ 371 (c)(1),
(2), (4) Date: Jun. 5, 2012

(87) PCT Pub. No.: WO2011/012527
PCT Pub. Date: Feb. 3, 2011

(65) Prior Publication Data
US 2012/0238605 A1    Sep. 20, 2012

(30) Foreign Application Priority Data

Jul. 29, 2009  (EP) .................................... 09290601
Feb. 26, 2010 (EP) .................................... 10305192

(51) Int. Cl.
*A61K 31/4418*    (2006.01)
*A61K 31/4409*    (2006.01)

(52) U.S. Cl.
CPC ....... *A61K 31/4409* (2013.01); *A61K 31/4418* (2013.01); *Y10S 514/822* (2013.01)

(58) Field of Classification Search
CPC ................................................ A61K 31/4409
See application file for complete search history.

(56) References Cited

FOREIGN PATENT DOCUMENTS

WO    WO 97/24118    7/1997

OTHER PUBLICATIONS

Guertin, Kevin R. et al., "The Discovery of the Factor Xa Inhibitor Otamixaban: From Lead Identification to Clinical Development" Current Medicinal Chemistry (2007), vol. 14, pp. 2471-2481.

Bassand, Jean-Pierre et al., "Guidelines for the diagnosis and treatment of non-ST-segment elevation acute coronary syndromes," European Heart Journal (2007), vol. 28, pp. 1598-1660.
Thygesen, Kristian et al., "Universal Definition of Myocardial Infarction," Journal of the American College of Cardiology (2007), vol. 50, No. 22, pp. 2175-2195.
Thygesen, Kristian et al., "Universal definition of myocardial infarction," European Heart Journal (2007), vol. 28, pp. 2525-2538.
Silber, Sigmund et al., "Guidelines for Percutaneous Coronary Interventions," European Heart Journal (2005), vol. 26, pp. 804-847.
Cohen, Marc et al., "Randomized, Double-Blind, Dose-Ranging Study of Otamixaban, a Novel, Parenteral, Short-Acting Direct Factor Xa Inhibitor, in Percutaneous Coronary Intervention," Circulation (2007), vol. 115, pp. 2642-2651.
Hinder, Markus et al., "Direct and rapid inhibition of factor Xa by otamixaban: A pharmacokinetic and pharmacodynamic investigation in patients with coronary artery disease," Clinical Pharmacology and Therapeutics (2006), vol. 80, pp. 691-702.
White, Harvey D. et al., "Acute myocardial infarction," The Lancet (2008), vol. 372, pp. 570-584.
European Search Report dated Nov. 16, 2009 issued in EP 09 29 0601.
International Search Report dated Aug. 24, 2010 issued in PCT/EP2010/060615.
Sabatine, M.S. et al. (Sep. 5, 2009). "Otamixaban for the Treatment of Patients with Non-ST-Elevation Acute Coronary Syndromes (SEPIA-ACS1 TIMI 42): A Randomised, Double-Blind, Active-Controlled, Phase 2 Trial," *The Lancet* 374:787-795.
Highlights of Prescribing Information for Lovenox (Enaxaparin Sodium Injection). 2009. Sanofi-Aventis US LLC. pp. 1-42.
Press Release. (Jun. 3, 2013) "Sanofi Provides Update on Phase 3 Studies of Two Investigational Compounds," Paris, France; 2 pages.
Written Opinion mailed Aug. 24, 2010, issued in PCT Application No. PCT/EP/2010/060615 filed on Feb. 3, 2011; 4 pages.

*Primary Examiner* — James D Anderson
*Assistant Examiner* — Gregg Polansky
(74) *Attorney, Agent, or Firm* — Morrison and Foerster LLP

(57) ABSTRACT

The invention relates to the use of (2R,3R)-2-(3-carbamimidoyl-benzyl)-3-[4-(1-oxy-pyridin-4-yl)benzoylamino]-butyric acid methyl ester or a pharmaceutically acceptable salt thereof, for the preparation of a medicament for use in non-ST elevation myocardial infarction, said treatment comprising administering a therapeutically effective amount of (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who is elderly and/or shows renal insufficiency and/or has a low body weight.

10 Claims, No Drawings

OTAMIXABAN FOR TREATMENT OF ELDERLY AND RENAL IMPAIRED NON-ST ELEVATION MYOCARDIAL INFARCTION PATIENTS

FIELD OF THE INVENTION

The present invention relates to the treatment of patients showing non-ST elevation myocardial infarction, who are elderly and/or show renal insufficiency, with a simple weight-adjusted dosage regimen improving patient safety and providing a net clinical benefit.

BACKGROUND OF THE INVENTION (2R,3R)-2-(3-Carbamimidoyl-benzyl)-3-[4-(1-oxy-pyridin-4-yl)benzoylamino]-butyric acid methyl ester, (CAS number 193153-04-7) has the International Nonproprietary Name otamixaban and shows the structure illustrated in Formula I:

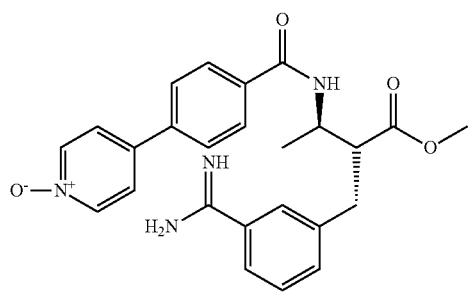

Formula I (2R,3R)-2-(3-Carbamimidoyl-benzyl)-3-[4-(1-oxy-pyridin-4-yl)benzoylamino]-butyric acid methyl ester (Otamixaban, Formula I) use in the preparation of a medicament for treating a patient suffering from, or subject to, conditions which can be ameliorated by the administration of an inhibitor of Factor Xa has been disclosed in WO97/24118.

Factor Xa is the penultimate enzyme in the coagulation cascade. Factor Xa (fXa) is a critical serine protease situated at the confluence of the intrinsic and extrinsic pathways of the blood coagulation cascade. FXa catalyses the conversion of prothrombin to thrombin via the prothrombinase complex. Its singular role in thrombin generation, coupled with its potentiating effects on clot formation render it an attractive target for therapeutic intervention.

Both free factor Xa and factor Xa assembled in the prothrombinase complex (Factor Xa, Factor Va, calcium and phospholipid) are inhibited by Otamixaban. Factor Xa inhibition is obtained by direct complex formation between the inhibitor and the enzyme and is therefore independent of the plasma co-factor antithrombin III. Effective factor Xa inhibition is achieved by administering the compound either by continuous intravenous infusion, bolus intravenous administration or any other parenteral route such that it achieves the desired effect of preventing the factor Xa induced formation of thrombin from prothrombin. In vivo experiments have demonstrated that Otamixaban is highly efficacious in rodent, canine and porcine models of thrombosis. In addition, recent clinical findings indicate that Otamixaban is efficacious, safe and well tolerated in humans and therefore has considerable potential for the treatment of acute coronary syndrome (K. R. Guertin and Yong-Mi Choi; 2007; Current Medicinal Chemistry, Vol. 14, No. 23; p. 2471-2481). Clinical findings in a dose-ranging clinical trial indicate that Otamixaban reduced prothrombin fragments 1+2 significantly more than unfractionated heparin at the highest dose regimen (Cohen et al., Circulation, Vol. 115, No. 20, May 2007, pages 2642-2651), but said clinical findings do not show data in comparison of age or renal impairment. Further clinical trials demonstrated that otamixaban induces dose-dependent, rapid direct factor Xa inhibition in patients with stable coronary artery disease who are taking their usual comedication, some of whom have mild renal impairment (Hinder et al., Clinical Pharmacology and Therapeutics, Vol. 80, No. 6, 2006, pages 691-702).

Acute coronary syndromes (ACS) are characterised by an imbalance between myocardial oxygen supply and demand. The most common cause is the reduced myocardial perfusion that results from coronary artery narrowing caused by a thrombus that has developed on a disrupted atherosclerotic plaque. Within the diagnosis of ACS two major subtypes can be distinguished that are non-ST elevation myocardial infarction (NSTE-ACS) and ST-elevation myocardial infarction (STE-MI). NSTE-ACS corresponds to a partial thrombotic occlusion of a coronary vessel with more or less pronounced ischemia. The main aim of treatment for these conditions is to prevent a sudden total occlusion of the arteries. STE-MI is characterised by a sudden total thrombotic occlusion of a coronary vessel resulting in ischemia of the heart. It needs to be treated urgently, within the initial 6-12 hours, and preferably 2 hours following the diagnosis. The goal is to restore patency (blood flow) of the occluded vessel.

Risk scores have been developed that regroup markers of the acute thrombotic process and other markers to identify patients with high-risk for total occlusion of vessels. In addition to the estimation of the risk, the assessment of the cardiac biomarker of necrosis, especially the cardiac troponins, are performed in order to select the treatment strategy of choice. It has been demonstrated during the last years that patients with moderate-to-high risk NSTE-ACS benefit from an early invasive strategy, where patients are brought early to a catheter lab (by the next day, or two) for angiography followed by a percutaneous coronary intervention (PCI). In recent US treatment guidelines for NSTE-ACS patients an invasive strategy is recommended for moderate-to-high risk patients while for lower risk patients a conservative strategy is preferred. However, timely access to invasive treatment is often more important for the decision than risk assessment. Furthermore, elderly and fragile patients are often not treated by invasive procedures due to increased risk for bleeding.

In all NSTE-ACS patients (with invasive or conservative strategy) a standard medical therapy is indicated including aspirin, clopidogrel and anticoagulant therapy. It appears beneficial to add an intravenous GPIIb/IIIa inhibitor, if an invasive strategy is planned in high-risk patients.

The primary discussions in medical literature today is focused on the moderate-to-high-risk NSTE-ACS patients, who are scheduled to undergo an early (≤48-72 h) diagnostic catheterization and coronary intervention. Aspirin, clopidogrel, GP IIb/IIIa inhibitors (including eptifibatide and abciximab), unfractionated heparin, bivalirudin, enoxaparin, fondaparinux are all recommended in the most recent guidelines indicating their recognition as standard of care for patients with moderate-to-high-risk NSTE-ACS.

Use of such a multi-tiered combination pharmacologic approach, however, has not been formally investigated and may result in increased risk of bleeding complications, greater complexity of treatment and increased costs. Further the presently used combination therapy of heparin and GP IIb/IIIa inhibitor is efficacious but causes bleeding in NSTE-ACS patients receiving dual oral antiplatelet therapy with aspirin and clopidogrel. Thus, the optimal anti-thrombotic regimen for moderate-to-high-risk for NSTE-ACS remains to be not found yet.

Further in the treatment of patients showing non-ST elevation myocardial infarction it is necessary that patients, who are elderly and/or show renal insufficiency (in the following NSTE-ACS risk patients) need a dose adjustment to avoid overdosing and bleeding. NSTE-ACS risk patients often show reduced compatibility to the used medicaments and have a higher risk of bleeding. Thus, NSTE-ACS risk patients have to be carefully adapted to the used anticoagulant therapy. Such an adaption is highly risky and could easily lead to a higher death rate and higher rate of myocardial infarction, because overdosing could not be avoided so easily.

It is an object of the present invention to find a medical treatment, which does not have the disadvantages mentioned and provides a reduction of death and/or myocardial infarction while retaining at least equal bleeding rates compared to standard therapy, in NSTE-ACS risk patients planned to undergo invasive management.

It has now unexpectedly been found that otamixaban offers improved management of NSTE-ACS risk patients. Unexpectedly, NSTE-ACS risk patients do not need a further adaption of their dosage regimen when treated with otamixaban. NSTE-ACS risk patients can be treated as the normal population having a dosage regimen which is solely weight-adjusted. Further patient safety is increased because the risk of a wrong dosage regimen does not occur. There is no need anymore for a different treatment between the normal patient and the NSTE-ACS risk patient. This is especially beneficial for elderly patients. There is also no need for dose adjustment of patients showing renal impairment (beyond weight-adjustment as in normal population) and this is especially beneficial in renal insufficient and severe renal insufficient patients. Further advantages of otamixaban are short initial half-life time, and mainly gastrointestinal excretion and a predictable relationship between pharmocokinetic and pharmacodynamic.

SUMMARY OF THE PRESENT INVENTION

The present invention provides the use of (2R,3R)-2-(3-carbamimidoyl-benzyl)-3-[4-(1-oxy-pyridin-4-yl)benzoylamino]-butyric acid methyl ester or a pharmaceutically acceptable salt thereof, for the preparation of a medicament for use in non-ST elevation myocardial infarction, said treatment comprising administering a therapeutically effective amount of (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who is elderly or shows renal insufficiency or has low body weight or is elderly and shows renal insufficiency or is elderly and has low body weight or is elderly, shows renal insufficiency and has low body weight.

DETAILED DESCRIPTION OF THE INVENTION

The invention therefore provides the use of (2R,3R)-2-(3-carbamimidoyl-benzyl)-3-[4-(1-oxy-pyridin-4-yl)benzoylamino]-butyric acid methyl ester or a pharmaceutically acceptable salt thereof, for the preparation of a medicament for use in non-ST elevation myocardial infarction, said treatment comprising administering a therapeutically effective amount of (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who is older than 65.

Terms used herein have the meanings defined in this specification.

"Elderly human patient" refers to patients beyond 65 years of age. A further group refers to patients from 65 to 75 or patients beyond 75 of age.

"Human patient with renal insufficiency" refers to patients showing creatinin clearance from 30 milliliter (ml) per min to 80 ml per min; a further group of patients with renal insufficiency showing creatinin clearance from 30 ml per min to 50 ml per min; a further group of patients with renal insufficiency showing creatinin clearance from 50 ml per min to 80 ml per min.

"Human patient with severe renal insufficiency" refers to patients showing creatinin clearance which is less than 30 ml per min. However, dialysis-dependent patients will be excluded from the current definition.

"i. v." refers to intra venous injection.

"low body weight patients" refers to patients of less than 50 kg. A further group refers to patients from 30 kg to 50 kg or patients from 40 kg to 50 kg.

"non-ST elevation myocardial infarction" refers to the definition of Myocardial Infarction based on ACC/AHA, ESC and WHF consensus; see also Guidelines for the diagnosis and treatment of non-ST segment elevation acute coronary syndromes; Eur Heart J, 2007, 28(13): 1598-1660; J Am Coll Cardiol, 2007; 50:2173-2195; Eur Heart J, 2007, 28: 2525-2538.

"Otamixaban" is the international nonproprietary name for (2R,3R)-2-(3-carbamimidoyl-benzyl)-3-[4-(1-oxy-pyridin-4-yl)benzoylamino]-butyric acid methyl ester as its hydrochloride salt.

"Pharmaceutically acceptable salt" is any non-toxic inorganic acid salt of the base compound (2R,3R)-2-(3-Carbamimidoyl-benzyl)-3-[4-(1-oxy-pyridin-4-yl)benzoylamino]-butyric acid methyl ester. Illustrative inorganic acids which form suitable salts include mineral acids, such as hydrochloric acid, hydrobromic acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. Preferably, the acid addition salt is derived from a mineral acid, with hydrochloric acid being preferred.

"TIMI" is the abbreviation for the "Thrombolysis in Myocardial Infarction" and refers to the classification of bleeding.

"Therapeutically effective amount" means an amount of the compound, which is effective in treating the named disorder or condition.

"Treat" or "treating" means any treatment, including, but not limited to, alleviating symptoms, eliminating the causation of the symptoms either on a temporary or permanent basis, or preventing or slowing the appearance of symptoms and progression of the named disorder or condition.

The synthesis of (2R,3R)-2-(3-carbamimidoyl-benzyl)-3-[4-(1-oxy-pyridin-4-yl)benzoylamino]-butyric acid methyl ester has been disclosed, and is accomplished by methods that are well known to those skilled in the art. For example International Application WO97/24118 discloses methods of synthesis.

In a further embodiment the invention relates to the use of (2R,3R)-2-(3-carbamimidoyl-benzyl)-3-[4-(1-oxy-pyridin-4-yl)benzoylamino]-butyric acid methyl ester or a pharmaceutically acceptable salt thereof, for the preparation of a medicament for use in non-ST elevation myocardial infarction said treatment comprising administering a therapeutically effective amount of (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who is older than 65 and shows renal insufficiency.

In a further embodiment the invention relates to the use of (2R,3R)-2-(3-carbamimidoyl-benzyl)-3-[4-(1-oxy-pyridin-4-yl)benzoylamino]-butyric acid methyl ester or a pharmaceutically acceptable salt thereof, for the preparation of a medicament for use in non-ST elevation myocardial infarction said treatment comprising administering a therapeutically effective amount of (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who shows renal insufficiency.

In a further embodiment the invention relates to the use of (2R,3R)-2-(3-carbamimidoyl-benzyl)-3-[4-(1-oxy-pyridin-4-yl)benzoylamino]-butyric acid methyl ester or a pharmaceutically acceptable salt thereof, for the preparation of a medicament for use in non-ST elevation myocardial infarction said treatment comprising administering a therapeutically effective amount of (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who shows severe renal insufficiency.

In a further embodiment the invention relates to the use of (2R,3R)-2-(3-carbamimidoyl-benzyl)-3-[4-(1-oxy-pyridin-4-yl)benzoylamino]-butyric acid methyl ester or a pharmaceutically acceptable salt thereof, for the preparation of a medicament for use in non-ST elevation myocardial infarction said treatment comprising administering a therapeutically effective amount of (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who has a body weight of less than 50 kg.

In a further embodiment the invention relates to the use of (2R,3R)-2-(3-carbamimidoyl-benzyl)-3-[4-(1-oxy-pyridin-4-yl)benzoylamino]-butyric acid methyl ester or a pharmaceutically acceptable salt thereof, for the preparation of a medicament for use in non-ST elevation myocardial infarction said treatment comprising administering a therapeutically effective amount of (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who has a body weight from 30 kg to 50 kg.

In a further embodiment the invention relates to the use of (2R,3R)-2-(3-carbamimidoyl-benzyl)-3-[4-(1-oxy-pyridin-4-yl)benzoylamino]-butyric acid methyl ester or a pharmaceutically acceptable salt thereof, for the preparation of a medicament for use in non-ST elevation myocardial infarction said treatment comprising administering a therapeutically effective amount of (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who has a body weight from 40 kg to 50 kg.

In a further embodiment the invention relates to (2R,3R)-2-(3-carbamimidoyl-benzyl)-3-[4-(1-oxy-pyridin-4-yl)benzoylamino]-butyric acid methyl ester or a pharmaceutically acceptable salt thereof, for use in the treatment of non-ST elevation myocardial infarction said treatment comprising administering (2R,3R)-2-(3-carbamimidoyl-benzyl)-3-[4-(1-oxy-pyridin-4-yl)benzoylamino]-butyric acid methyl ester or a pharmaceutically acceptable salt thereof to a human patient, who is older than 65.

In a further embodiment the invention relates to (2R,3R)-2-(3-carbamimidoyl-benzyl)-3-[4-(1-oxy-pyridin-4-yl)benzoylamino]-butyric acid methyl ester or a pharmaceutically acceptable salt thereof, for use in the treatment of non-ST elevation myocardial infarction said treatment comprising administering (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who is older than 65 and shows renal insufficiency.

In a further embodiment the invention relates to (2R,3R)-2-(3-carbamimidoyl-benzyl)-3-[4-(1-oxy-pyridin-4-yl)benzoylamino]-butyric acid methyl ester or a pharmaceutically acceptable salt thereof, for use in the treatment of non-ST elevation myocardial infarction said treatment comprising administering (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who shows renal insufficiency.

In a further embodiment the invention relates to (2R,3R)-2-(3-carbamimidoyl-benzyl)-3-[4-(1-oxy-pyridin-4-yl)benzoylamino]-butyric acid methyl ester or a pharmaceutically acceptable salt thereof, for use in the treatment of non-ST elevation myocardial infarction said treatment comprising administering (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who shows severe renal insufficiency.

In a further embodiment the invention relates to (2R,3R)-2-(3-carbamimidoyl-benzyl)-3-[4-(1-oxy-pyridin-4-yl)benzoylamino]-butyric acid methyl ester or a pharmaceutically acceptable salt thereof, for use in the treatment of non-ST elevation myocardial infarction said treatment comprising administering (2R,3R)-2-(3-Carbamimidoyl-benzyl)-3-[4-(1-oxy-pyridin-4-yl)benzoylamino]-butyric acid methyl ester or a pharmaceutically acceptable salt thereof to a human patient, who has a low body weight.

The relative amounts of otamixaban and acid in the salts may vary and depends, for example, on the particular acid selected and the methods employed in preparing the salts. Preferably, the salts of the present invention comprise about one equivalent of acid for about each equivalent of otamixaban.

The acid addition salts of otamixaban may be prepared by dissolving the free base in aqueous or aqueous-alcohol solution or other suitable solvents containing the appropriate acid or to which the appropriate acid is added, and isolating the salt by evaporating the solution, or by reacting the free base and acid in an organic solvent, in which case the salt may separate directly and/or may be obtained by concentration of the solution.

In general in the adult population, suitable doses may range from 0.7 mg/Kg body weight/h to 1.4 mg/Kg body weight/h. Further suitable doses may range from 0.8 mg/Kg body weight/h to 1.2 mg/Kg body weight/h. Also a suitable dose balancing patient safety and efficacy will be a dose close to 0.1 mg/kg body weight/h after i.v. bolus of approximately 0.08 mg/kg body weight.

In general in the adult population, suitable doses may range from 0.07 mg/Kg body weight/h to 0.14 mg/Kg body weight/h. Further suitable doses may range from 0.08 mg/Kg body weight/h to 0.12 mg/Kg body weight/h.

Sterile injectable solutions may be prepared by incorporating otamixaban in the required amounts, in the appropriate solvent, with various of the other ingredients enumerated herein, as required, followed by filtered sterilization. Generally, dispersions may be prepared by incorporating the sterilized active ingredient into a sterile vehicle which contains the dispersion medium and any other required ingredients. In the case of sterile powders for the preparation of sterile injectable solutions, the preferred methods of preparation may include vacuum drying and the freeze drying technique which may yield a powder of the active ingredient, plus any additional desired ingredient from the previously sterile-filtered solution thereof.

Liquid compositions may also contain other components routinely utilized in formulating pharmaceutical compositions. One example of such components is lecithin. Its use in compositions of the invention as an emulsifying agent may range from about 0.05 to about 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

In general, water, a suitable oil, saline, aqueous dextrose (glucose), and related sugar solutions and glycols, such as propylene glycol or polyethylene glycols may be suitable carriers for parenteral solutions. Solutions for parenteral solutions may be prepared by dissolving Otamixaban in the carrier and, if necessary, adding buffering substances. Antioxidizing agents, such as sodium bisulfite, sodium sulfite, or ascorbic acid either alone or combined, may be suitable stabilizing agents. Citric acid and its salts and sodium EDTA may also be employed. Parenteral solutions may also contain preservatives, such as benzalkonium chloride, methyl- or propyl-paraben and chlorobutanol.

Useful pharmaceutical dosage-forms for administration of otamixaban can be illustrated as follows:

Suspensions

An aqueous suspension may be prepared for oral administration so that each 5 mL contains 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection may be prepared by stirring 1.5% by weight of active ingredient in 10% by volume propylene glycol and water. The solution may be sterilized by commonly used techniques.

The following non-limiting examples illustrate the inventors' preferred methods for preparing and using the pharmaceutical compositions of the present invention.

EXAMPLES

Example 1

Preparation of Compound (III)

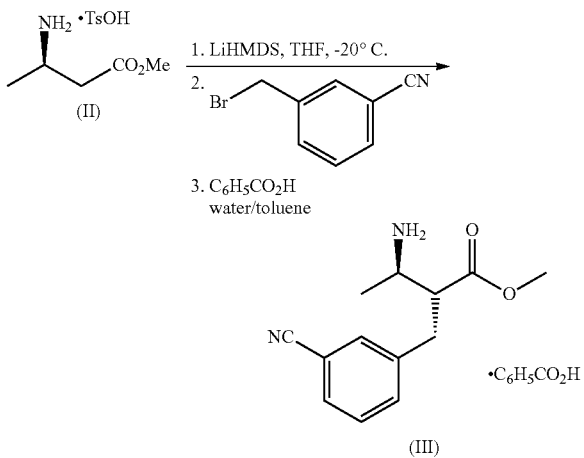

TsOH is p-Toluenesulfonic acid with the formula $CH_3C_6H_4SO_3H$. TsOH refers to the monohydrate. To a reactor were charged Compound (II) (100.0 g) and anhydrous tetrahydrofuran (THF) (320 g). The resulting suspension was cooled down to −20±3° C. and lithium hexamethyldisilazide (LiHMDS) (475.6 grams, 1.3 M solution in THF) was added over 55 minutes and stirred for 20 minutes at −20±3° C. A solution of α-bromo-m-tolunitrile in THF (65.1 g in 181 g of THF) was then charged into the reactor over 40 minutes while maintaining the temperature at −20±3° C. and stirred for another 30 minutes. Benzoic acid (126.6 grams) was charged as a solid to the reactor. Water (1000 g) was then added and mixture distilled at a 65±3° C. jacket temperature and 200-233 mbar vacuum. After distilling to a constant pot temperature of 57° C. and constant head temperature of 45° C., the distillation was stopped. Toluene (432 g) was added to the hot solution and stirred while cooling down to 10±2° C. The resulting suspension was then filtered and the filter cake washed with water (250 grams) and toluene (432 grams). Compound (III) was dried at 45-50° C. at ~350 mbar vacuum under a nitrogen stream for 24 hours until constant weight. The isolated solid weighed 76.0 grams (62.0% yield).

Example 2

Preparation of Compound (V)

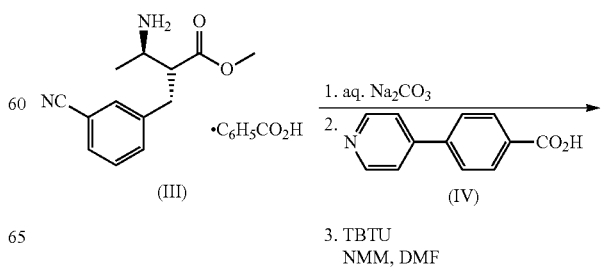

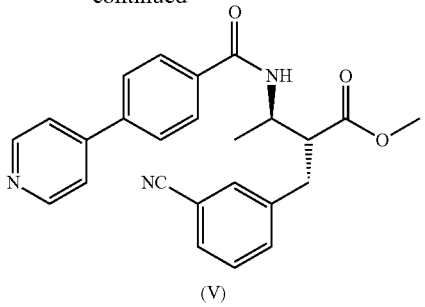

(V)

Compound (III) was partitioned between dichloromethane and aqueous sodium carbonate. The organic phase (containing the free base of (III)) was washed with additional aqueous sodium carbonate and was distilled under reduced pressure and solvent exchanged with dimethylformamide (DMF). This solution was assayed for wt/wt content of (III). To a suspension of (IV) (1.0 equivalent vs. (III)) in DMF were added 2 equivalents of 4-methylmorpholine and 1.1 equivalents of O-Benztriazol-1-yl-N,N,N',N'-tetramethyluronium tetrafluoroborate (TBTU). This mixture was stirred at ambient temperature until ester activation was complete (about 90 minutes). The DMF solution of Compound (III) (1 equivalent) was added and the resulting solution stirred overnight after which HPLC indicated that the reaction was complete. Water was added at 75° C. and the mixture was cooled to crystallize the product. The mixture was cooled to 5° C., filtered, and the filter cake was washed with water. The product was dried under reduced pressure at 70° C.

Example 3

Preparation of Compound (VI)

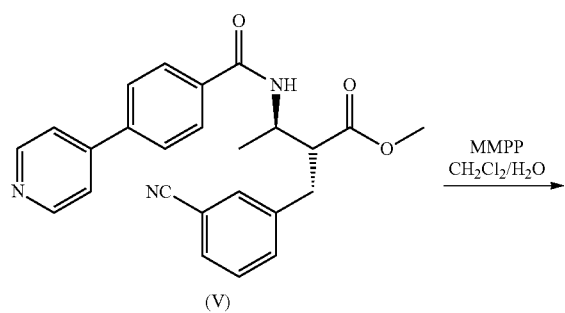

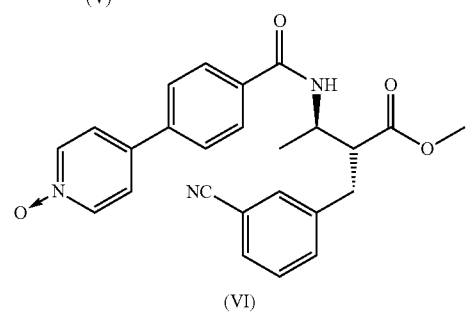

(VI)

In a well-stirred reactor, 45 g of Compound (V) in 450 mL dichloromethane was reacted for at least 5 hours with 61 g of magnesium monoperoxyphthalate (66.4% based on available oxygen, 1.5 eq.) in 450 g of water until the reaction was complete. The phases were separated and the organic phase was washed successively with equal volumes of water, a 5% aqueous sodium bicarbonate solution, and water. The resulting solution was concentrated to an approximately 40 wt % solution and diluted with 180 g of methyl isobutyl ketone (MIBK). Further distillation to remove residual dichloromethane, seeding with appropriate crystals, and cooling gave the product as a crystalline solid. The crystals were filtered, rinsed with 30 g of MIBK, and dried at 50° C. under reduced pressure to give 41.8 g of Compound (VI) (89.3% yield).

Example 4

Preparation of Compound (I)

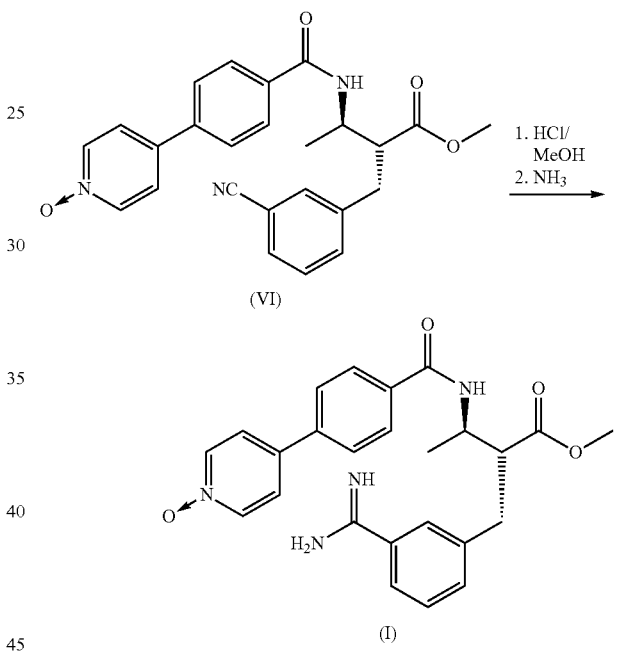

To a 200-mL jacketed reaction flask were charged Compound (VI) (50.0 g, 116 mmol) and methanol (50 mL). This mixture was cooled to −5° C. and sealed after establishing a partial vacuum (about 100 torr). Anhydrous HCl (52.2 g, 1.43 mol) was added while maintaining the reaction temperature at less than 0° C. The reaction was stirred at 0±1° C. under closed conditions. After 16 hours, the reaction was complete (less than 2 A % (VI) by HPLC). To the intermediate product solution was added anhydrous methanol (100 mL) while maintaining the temperature at less than 5° C. The solution was treated with NH₃ (27.7 g, 1.62 mol) keeping the temperature less than 0° C. Before allowing the mixture to warm to room temperature, a pH check was made of an aliquot dissolved in DI water (a pH of 8-10 indicates a sufficient charge of ammonia). The reaction was stirred at 20° C. overnight at which point the reaction was complete.

Example 5

The following results are based on a randomized, double-blind triple-dummy trial to compare otamixaban to Unfractionated Heparin+eptifibatide, in patients with Unstable angina/Non ST segment Elevation Myocardial infarction scheduled to undergo an early invasive strategy.

Study Population:

Patient with non STE-segment elevation Acute Coronary Syndrome with the following symptoms:

Ischemic discomfort (i.e., ischemic chest pain or equivalent) at rest 0 minutes within 24 hours of randomization

AND one of the two following criteria of non-ST elevation ACS:

New ST-segment depression≥0.1 mV (≥1 mm), or transient (<30 minutes) ST-segment elevation≥0.1 mV (≥1 mm) in at least 2 contiguous leads on the ECG, OR Elevation of cardiac biomarkers within 24 hours of randomization, defined as elevated troponin T, troponin I, or CK-MB level above upper limit of normal

AND planned to have a coronary angiography (followed, when indicated, by percutaneous coronary intervention (PCI)) on Day 1 (day of randomization) to Day 3

AND

Informed consent obtained in writing

Investigational Products:

Otamixaban/placebo;

UFH/placebo;

eptifibatide/placebo

Formulation: i.V. solution

Route(s) of administration: Intravenous: bolus (Bol) followed by continuous infusion (I)

Dose Regimen:

Otamixaban arm: (Bol) 0.080 mg/Kg (I) 0.035 mg/Kg/h or 0.070 mg/Kg/h or 0.105 mg/Kg/h or 0.175 mg/Kg/h If a patient requires Coronary Artery Bypass Surgery (CABG), blinded treatment should be permanently discontinued, with Drug A (otamixaban/placebo) and Drug B (UFH/placebo) discontinued at least 6 hours prior to the surgery, if possible. Patient should be treated as per the site's usual standard of care.

Comparator: UFH+Eptifibatide

UFH: 60 IU/Kg as IV bolus (max 400 IU) followed by an IV infusion of 12 U/Kg/h (max 1000 IU/h) to maintain a PTT at 1.5 to 2.0 times control and at the time of the PCI additional boluses needed if the ACT is not in the range of 200-250 seconds. NB: In order for the study to be blinded, all aPTTs and ACTs performed in order to adjust Drug B (UFH/placebo) dosing will be performed using an encrypted Hemochron Signature Elite machine (or as a back-up, a local device with a third-party unblinded healthcare professional).

Eptifibatide: a single bolus of 180 mcg/kg followed by an infusion of 2 mcg/kg/min. In patients with CrCl<50 mL/min the infusion rate will be decreased to 1 mcg/kg/min.

Bailout Eptifibatide:

In the otamixaban group: a single bolus of eptifibatide (180 mcg/kg) followed by an infusion of open label eptifibatide.

In the UFH+eptifibatide group: a single bolus of eptifibatide placebo followed by an infusion of open label eptifibatide.

In both groups:

Drug C (infusion of eptifibatide/placebo) is stopped.

the infusion rate of open-label eptifibatide is 2 mcg/kg/min (in patients with CrCl<50 mL/min the infusion rate will be decreased to 1 mcg/kg/min).

Primary endpoint: Adjudicated composite of all-cause death and new myocardial infarction (MI) within 7 days following randomization Secondary End Points Adjudicated composite of all-cause death and new myocardial infarction (MI) within 30 days following randomization Adjudicated Death all cause within 30 days following randomization Safety:

Non-CABG TIMI significant (Major+Minor) bleeding adjudicated by a blinded Clinical Events Adjudication Committee (CEAC) at Day 7.

Non-CABG TIMI Major bleeding adjudicated by a blinded Clinical Events Adjudication Committee (CEAC) at Day 7.

CABG-related bleeding adjudicated by a blinded Clinical Events Adjudication Committee (CEAC) at Day 7.

TIMI Major Bleeding (Non CABG+CABG) adjudicated by a blinded Clinical Events Adjudication Committee (CEAC) at Day 7.

Adjudicated TIMI Minor bleedings at Day 7

Adjudicated Thrombotic and non-thrombotic procedural complications during the index PCI (including abrupt or threatened closure, new intracoronary thrombus, side branch closure, distal embolization, noreflow, thrombus in catheter or adherent to guidewire, coronary dissection with decreased flow, difficulty in reaching or crossing lesion, unplanned stent use, suboptimal results, coronary perforation, tamponade). All the above events will be adjudicated by a blinded Independent Adjudication Committee.

Efficacy End Point:

The events will be adjudicated by a blinded independent adjudication committee. Since the goal of treating acute ACS without persistent ST segment elevation is to prevent associated morbidity and mortality, death and myocardial infarction are considered to be the clinically most meaningful endpoints in therapeutic studies, whereas recurrent ischemia or refractory angina is of more uncertain clinical relevance (EMEA/CPCP/EWP/570/98; February 2008).

The primary endpoint has been defined as the double clinical efficacy endpoint (all cause death and Myocardial Infarction based on centrally adjudicated data) that will be assessed at Day 7. Further estimation of this endpoint will be done at Day 30, Day 90 and Day 180 (end of the follow up) to check persistence of effect as recommended by the EMEA guideline (EMEA/CPCP/EWP/570/98; February 2008).

Definitions of Primary Efficacy Components:

All cause mortality (e.g. to consider all deaths regardless of cause) is the preferred and more conservative approach to the analysis of death in clinical trials since the classification of the mode of death is sometimes fraught with difficulties. As a component of a combined efficacy endpoint, all cause mortality provides very valid information about the clinical usefulness of the new drug.

Myocardial Infarction

Myocardial Infarction is considered to be a hard component of a combined efficacy endpoint for confirmatory clinical trials. The definition of Myocardial Infarction will be based on ACC/AHA, ESC and WHF consensus (J Am Coll Cardiol, 2007; 50:2173-2195; Eur Heart J, 2007, 28: 2525-2538):

In order to meet the criteria for the endpoint myocardial infarction, the myocardial infarction must be distinct from the index event. Four situations are described:

Patients in whom biomarkers are documented not to be elevated for at least 12 hours after the last episode of ischemia related to their index presentation or in whom biomarkers have been documented to return to normal after the index event, Patients in whom biomarkers from the index event remain elevated at the time of onset of the potential new MI, Patients in whom biomarkers are not elevated, but less than 12 hours has elapsed since their last episode of ischemia related to their index presentation, Within 48 hours after PCI:

Within 72 hours after CABG

NOTE: the best test to diagnose a MI are the troponin (I or T). If troponin assay is not available the best alternative is CKMB (measured by mass assay). Measurement of total CK is not recommended for the diagnosis of MI.

Rational for the Choice of the Comparator and the Duration of Treatment

Comparator Arm:

In moderate to high risk UA/NSTEMI patients managed by an early invasive strategy the guidelines (Eur Heart J, 2007, 28(13): 1598-1660) recommend a treatment with an anticoagulant, and both oral (aspirin±clopidogrel) and parenteral (GP IIb/IIIa inhibitors) antiplatelets agents.

Choice of the Anticoagulant:

UFH is the only anticoagulant recommended by both the European and the North American Guidelines with an IA grade, whereas they differ concerning the grading of enoxaparin (IIB for the European guideline and Ia for the North American guidelines). The dose of UFH will be the one recommended by the guidelines (Eur Heart J, 2005, 26: 804-847).

The choice of the GPIIb/IIIA inhibitor was based on the timing of administration and on the use of the GPIIb/IIIa inhibitor in the current practice. The guidelines recommend to initiate the GP IIb/IIIa inhibitor treatment immediately in case of moderate to high risk pattern with eptifibatide or tirofiban (Eur Heart J, 2007, 28(13): 1598-1660). Eptifibatide is more commonly used than tirofiban (Aggrastat®) and will be used in this study according to its approved regimen with an upstream start. Eptifibatide will be given as per the approved label (dose regimen and duration of treatment).

Duration of Treatment:

The duration of treatment will be the same as in the phase 2 (SEPIA ACS):

The angiography/PCI will be performed at least 2 hours after the start of study drug (otamixaban/UFH) and maximum up to Day 3 (Day 1=day of randomization)

UFH and otamixaban will be stopped at the end of the PCI, as per the ACC/ESC guidelines (Eur Heart J, 2005, 26: 804-847) unless an anticoagulant is indicated (recurrent ischemia, atrial fibrillation or left ventricular thrombus)

The maximum duration of treatment with otamixaban/UFH (Drug NB) will be 96 hours and they should not be given after Day 4.

Eptifibatide (Drug C) will be continued up to 18-24 hour post PCI or hospital discharge, whichever comes first (for a maximum of 96 hours of treatment—as per its label) and should not be given after Day 4.

The following table 1 shows the efficacy results for elderly patients.

TABLE 1

| Age [years] | Ota.: 0.035 [mg/Kg/h] (N = 125) | Ota.: 0.070 [mg/Kg/h] (N = 676) | Ota.: 0.105 [mg/Kg/h] (N = 662) | Ota.: 0.140 [mg/Kg/h] (N = 658) | Ota.: 0.175 [mg/Kg/h] (N = 671) | UFH/ Eptifibatide (N = 449) |
|---|---|---|---|---|---|---|
| <65 | 5/74 (6.8%) | 16/394 (4.1%) | 8/394 (2.0%) | 9/383 (2.3%) | 16/401 (4.0%) | 16/278 (5.8%) |
| 65 to 75 | 2/33 (6.1%) | 11/186 (5.9%) | 11/170 (6.5%) | 9/182 (4.9%) | 7/164 (4.3%) | 5/110 (4.5%) |
| Older than 75 | 2/18 (11.1%) | 4/96 (4.2%) | 6/98 (6.1%) | 6/93 (6.5%) | 6/106 (5.7%) | 7/61 (11.5%) |

<65 means less than age 65
N means number of patients
Ota. means the compound otamixaban and the used amount in the continuous infusion in mg/Kg/h The results show e.g. in case 5/74 (6.8%) that 74 patients are in the group of less than 65 years and that 5 patients showed the endpoint of the study. In brackets is the number of patients with endpoint in comparison with the whole number of patients in this age group.

The following table 2 shows the safety results for elderly patients, who show bleeding through day 7.

TABLE 2

| Age [years] | Ota.: 0.035 [mg/Kg/h] (N = 122) | Ota.: 0.070 [mg/Kg/h] (N = 669) | Ota.: 0.105 [mg/Kg/h] (N = 651) | Ota.: 0.140 [mg/Kg/h] (N = 651) | Ota.: 0.175 [mg/Kg/h] (N = 664) | UFH/ Eptifibatide (N = 448) |
|---|---|---|---|---|---|---|
| <65 | 0/74 | 3/393 (0.8%) | 7/387 (1.8%) | 6/380 (1.6%) | 4/396 (1.0%) | 4/277 (1.4%) |
| 65 to 75 | 0/31 | 3/184 (1.6%) | 1/166 (0.6%) | 6/179 (3.4%) | 9/163 (5.5%) | 1/110 (0.9%) |
| Older than 75 | 1/17 (5.9%) | 2/92 (2.2%) | 3/98 (3.1%) | 4/92 (4.3%) | 13/105 (12.4%) | 3/61 (4.9%) |

<65 means less than age 65
N means number of patients
Ota. means the compound otamixaban and the used amount in the continuous infusion in mg/Kg/h The results show e.g. in case 3/393 (0.8%) that 393 patients are in the group of less than 65 years and that 3 patients showed bleeding. In brackets is the number of patients with bleeding in comparison with the whole number of patients in this age group.

The following table 3 shows the efficacy results for patients with renal insufficiency.

Balancing efficacy and safety, the optimal otamixaban dose may be between dose arm 2 (0.070 mg/kg/h) and dose arm 3 (0.105 mg/kg/h).

Subgroup analysis has been performed and demonstrated consistency of the clinical results within demographic sub-

TABLE 3

| Creatinine clearance [ml/min] | Ota.: 0.035 [mg/Kg/h] (N = 122) | Ota.: 0.070 [mg/Kg/h] (N = 669) | Ota.: 0.105 [mg/Kg/h] (N = 651) | Ota.: 0.140 [mg/Kg/h] (N = 651) | Ota.: 0.175 [mg/Kg/h] (N = 664) | UFH/ Eptifibatide (N = 448) |
|---|---|---|---|---|---|---|
| <30 | 0/2 | 0/2 | 0/0 | 3/4 (75.0%) | 0/3 | 0/1 |
| 30 to 50 | 0/7 | 5/54 (9.3%) | 8/46 (17.4%) | 4/46 (8.7%) | 3/48 (6.3%) | 1/33 (3.0%) |
| 50 to 80 | 5/29 (17.2%) | 9/188 (4.8%) | 5/189 (2.6%) | 6/192 (3.1%) | 8/178 (4.5%) | 11/119 (9.2%) |
| more than 80 | 3/79 (3.8%) | 14/382 (3.7%) | 10/378 (2.6%) | 9/372 (2.4%) | 14/392 (3.6%) | 16/268 (6.0%) |

<30 means less than ml/min creatinine clearance
N means number of patients
Ota. means the compound otamixaban and the used amount in the continuous infusion in mg/Kg/h The results show e.g. in case 5/54 (9.3%) that 54 patients are in the group of Creatinine clearance from 30 to 50 ml/min and that 5 patients showed the endpoint of the study. In brackets is the number of patients with endpoint in comparison with the whole number of patients in this age group.

The following table 4 shows the safety results for patients with renal insufficiency, who show bleeding through day 7.

TABLE 4

| Creatinine clearance [ml/min] | Ota.: 0.035 [mg/Kg/h] (N = 122) | Ota.: 0.070 [mg/Kg/h] (N = 669) | Ota.: 0.105 [mg/Kg/h] (N = 651) | Ota.: 0.140 [mg/Kg/h] (N = 651) | Ota.: 0.175 [mg/Kg/h] (N = 664) | UFH/ Eptifibatide (N = 448) |
|---|---|---|---|---|---|---|
| <30 | 0/2 | 0/2 | 0/0 | 0/4 | 0/3 | 0/1 |
| 30 to 50 | 1/7 (14.3%) | 1/54 (1.9%) | 1/46 (2.2%) | 3/46 (6.5%) | 2/48 (4.2%) | 0/33 |
| 50 to 80 | 0/29 | 4/188 (2.1%) | 4/189 (2.1%) | 5/192 (2.6%) | 14/178 (7.9%) | 6/119 (5.0%) |
| more than 80 | 0/79 | 3/382 (0.8%) | 5/378 (1.3%) | 5/372 (1.3%) | 7/392 (1.8%) | 1/268 (0.4%) |

N means number of patients
Ota. means the compound otamixaban and the used amount in the continuous infusion in mg/Kg/h The results show e.g. in case 4/188 (2.1%) that 188 patients are in the group of Creatinine clearance from 50 to 80 ml/min and that 4 patients showed bleeding. In brackets is the number of patients with bleeding in comparison with the whole number of patients in this age group.

The clinical data show based on the primary efficacy endpoint, primary safety endpoint and thrombotic complication rate:

Otamixaban dose arms 0.035 mg/Kg/h and 0.070 mg/Kg/h (dose arms 1 and 2) offer inadequate anticoagulation based on rates of bailout and thrombotic complications.

Otamixaban dose arms from 0.105 to 0.175 mg/Kg/h (dose arm 3 to 5) had rates of primary endpoint that tended to be 31-41% lower than UFH+Eptifibatide. This benefit was primarily in death or myocardial infarction (MI) (42% to 48% lower), with no demonstrable effect on urgent revascularization or need for bailout.

Otamixaban dose arm 5 cause excessive TIMI significant bleeding.

As compared to UFH+eptifibatide, bleeding risk with dose arm 3 was associated with numerically higher rates of TIMI major, TIMI minimal but lower rates of TIMI minor (for patients without TIMI major).

Given the fact that there were more thrombotic complication in dose 2 than 3, and that thrombotic complications would be a serious concern (with potential impact on the Primary efficacy endpoint of death plus MI—in the phase 3) the preferred dose appears to be at about 0.1 mg/Kg/h (closer to dose 3).

In order to verify that this dose would also be appropriate in patient subgroups (elderly patients, patients with renal insufficiency and low body weight patients) pharmacokinetic analysis have been performed on those subgroups:

in general no impact of age, creatinine clearance level or body weight was observed for the concentration of otamixaban, except for dose 4 where higher concentration were observed in patients with renal impairment and in elderly patients, but this was not observed for the other dose group so was probably play of chance.

The conclusion of those subgroup pharmacokinetic analysis are that with a dose selected at about 0.1 mg/kg/h no dose adjustment is necessary in elderly patients, patient with renal impairment or patients with low body weight.

The invention claimed is:

1. A method of treating non-ST elevation myocardial infarction in a human patient in need thereof, comprising administering to said patient (2R,3R)-2-(3-carbamimidoyl-benzyl)-3-[4-(1-oxy-pyridin-4-yl)benzoylamino]-butyric acid methyl ester or a pharmaceutically acceptable salt thereof, in an amount between 0.070 mg/kg body weight/h and 0.105 mg/kg body weight/h of said patient, wherein the said patient is older than 75 years old and has non-ST elevation myocardial infarction.

2. The method according to claim 1 wherein the pharmaceutically acceptable salt is a hydrochloride salt.

3. The method according to claim 1 wherein said amount is at about 0.1 mg/Kg body weight/h.

4. The method according to claim 1 wherein the patient shows a creatinine clearance from 30 milliliter per min to 50 milliliter per min.

5. The method according to claim 1 wherein the patient shows a creatinine clearance from 50 milliliter per min to 80 milliliter per min.

6. The method according to claim 1 wherein the patient shows a creatinine clearance of less than 30 milliliter per min.

7. The method according to claim 1 wherein the patient has a body weight of less than 50 kg.

8. A method of treating non-ST elevation myocardial infarction in a human patient comprising administering to said patient (2R,3R)-2-(3-carbamimidoyl-benzyl)-3[4-(1-oxy-pyridin-4-yl)benzoylamino]-butyric acid methyl ester or a pharmaceutically acceptable salt thereof, in an amount between 0.070 mg/kg body weight/h and 0.105 mg/kg body weight/h of said patient, wherein said patient shows renal insufficiency and a creatinine clearance of less than 30 milliliter per min and has non-ST elevation myocardial infarction.

9. The method according to claim 1 wherein the patient has a body weight from 30 kg to 50 kg.

10. The method according to claim 8 wherein said amount is at about 0.1 mg/Kg body weight/h.

* * * * *